United States Patent

Yates

[11] Patent Number: 5,741,500
[45] Date of Patent: Apr. 21, 1998

[54] GUM GROWTH PAD

[76] Inventor: Alayne Yates, 4176 Round Top Dr., Honolulu, Hi. 96822

[21] Appl. No.: 680,135
[22] Filed: Jul. 15, 1996
[51] Int. Cl.[6] .................................................. A61K 9/70
[52] U.S. Cl. .................................. 424/404; 424/402
[58] Field of Search ................................ 424/426, 435, 424/444, 402, 404; 604/77; 128/848, 859

[56] References Cited

U.S. PATENT DOCUMENTS 5,326,685  7/1994  Gaglio et al. ........................ 433/215

*Primary Examiner*—Thurman K. Page
*Assistant Examiner*—Kathryne E. Shelborne
*Attorney, Agent, or Firm*—Michael I. Kroll

[57] ABSTRACT

A gum growth pad (10) comprising a nonporous first layer (12). An absorbent second layer (14) is placed upon the nonporous first layer (12). A growth medication (16) in a liquid form is impregnated within the absorbent second layer (14) and then dried. A semi-permeable third layer (18) covers the absorbent second layer (14) with the dried gum tissue growth medication (16). A facility (20) is for sealing the nonporous first layer (12) to the semi-permeable third layer (18) about a periphery thereof.

18 Claims, 2 Drawing Sheets

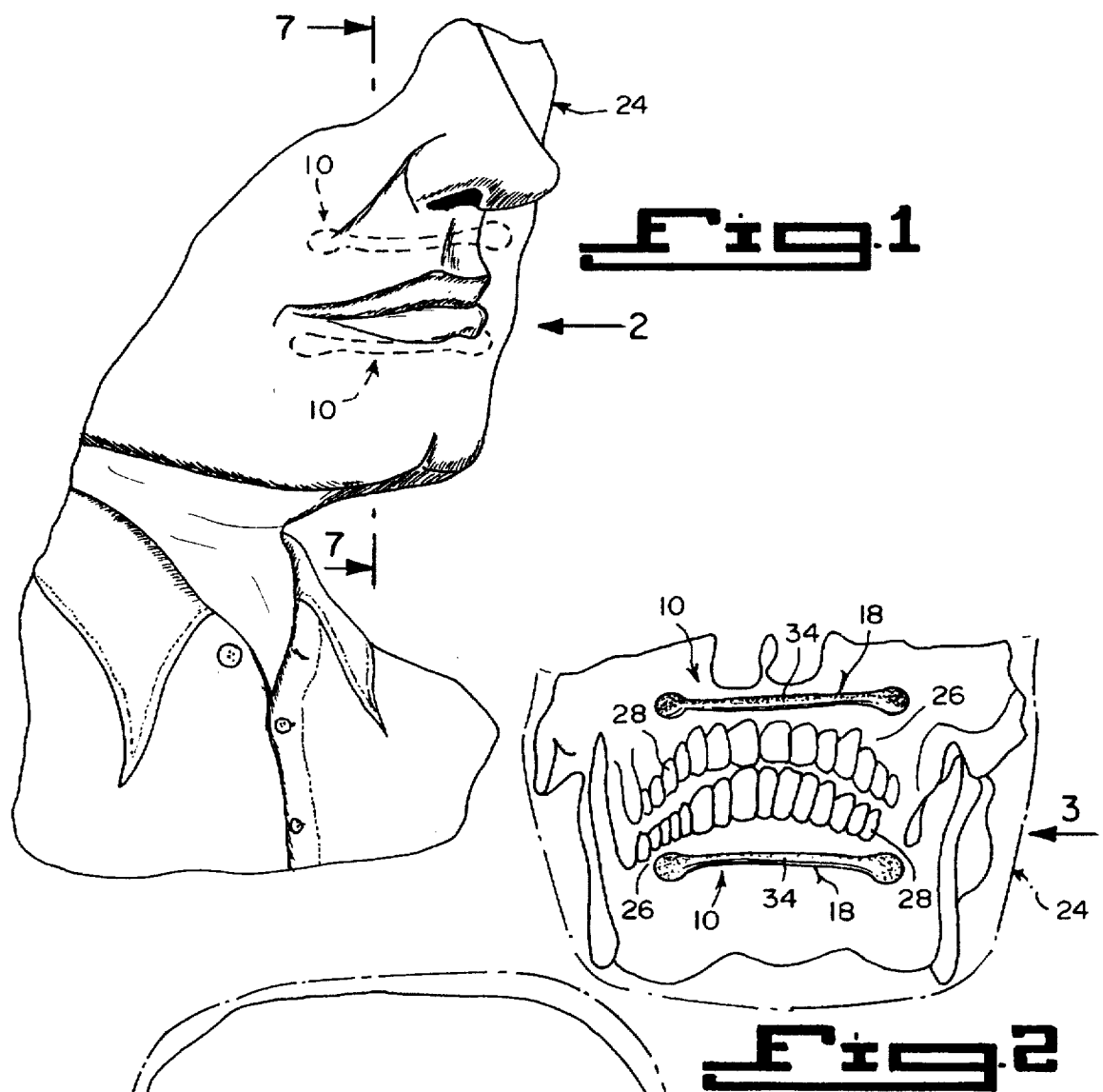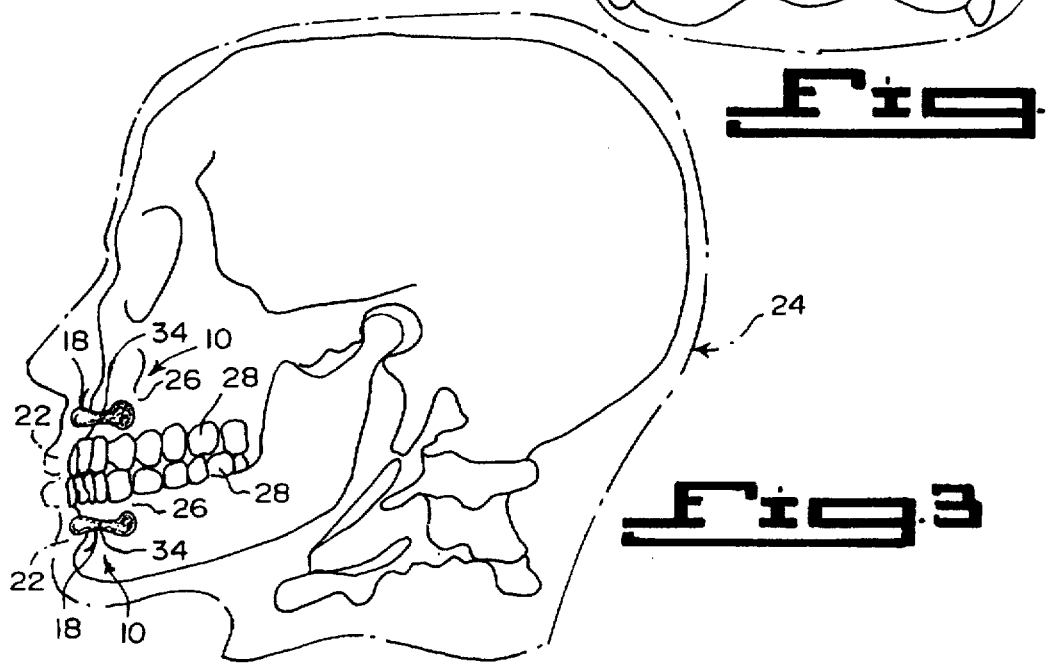

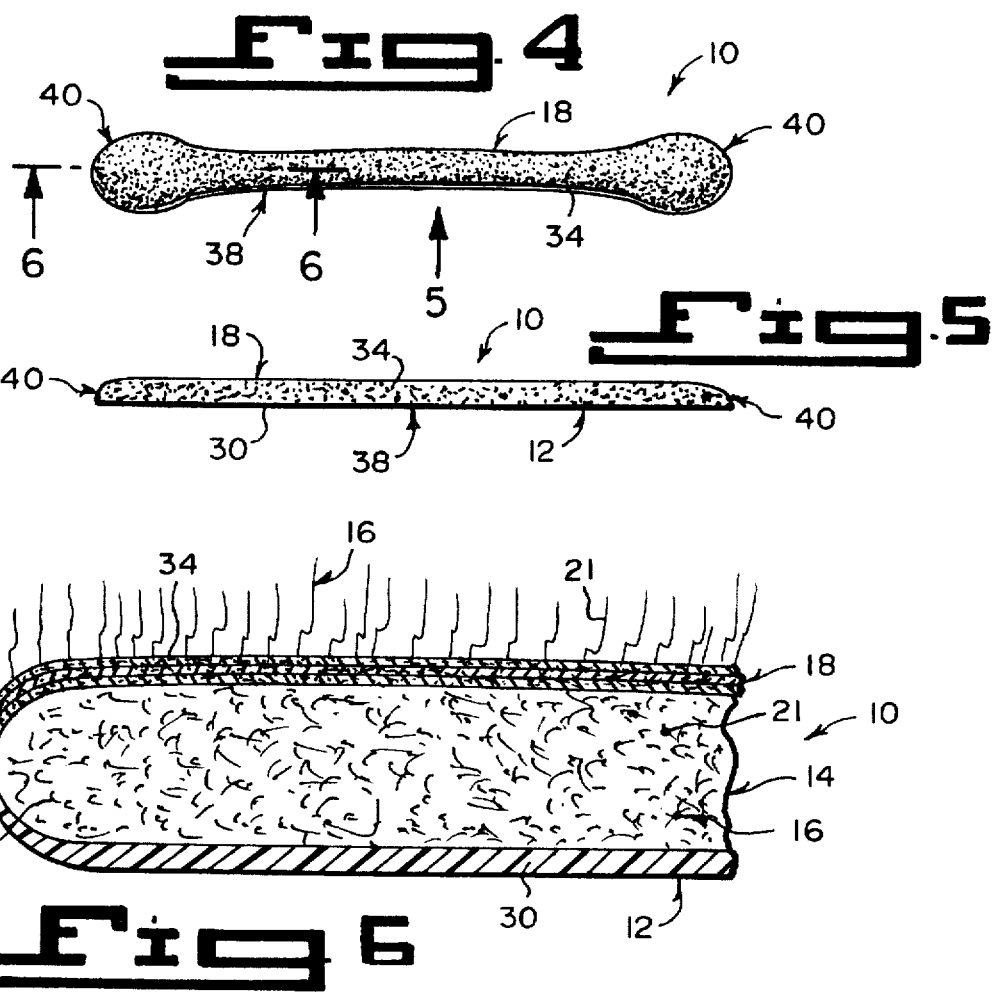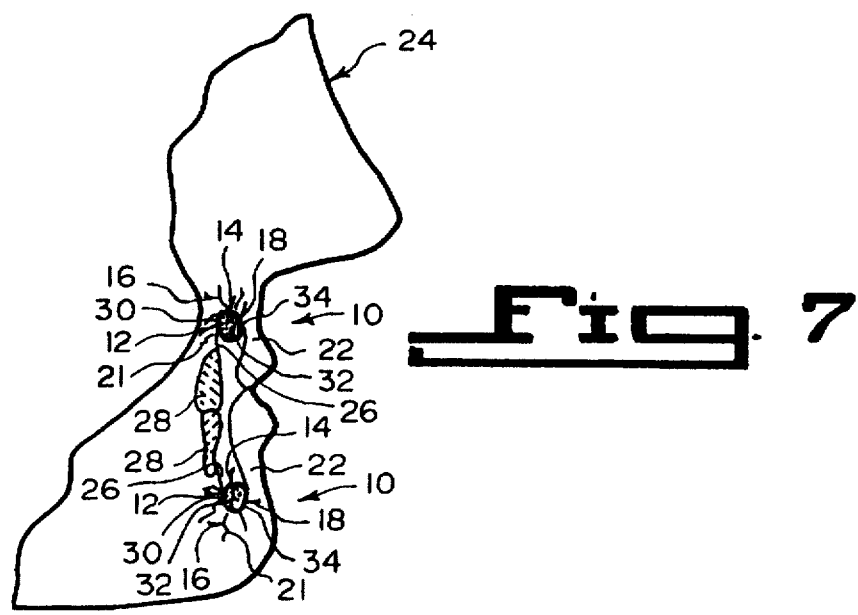

GUM GROWTH PAD

BACKGROUND OF THE INVENTION

1. Field of the Invention

The instant invention relates generally to holding devices and more specifically it relates to a gum growth pad.

2. Description of the Prior Art

Numerous holding devices have been provided in prior art. For example, U.S. Pat. Nos. 3,510,053 to Focke; 5,197,882 to Jernberg; 5,267,862 to Parker and 5,326,685 to Gaglio et al. are all illustrative of such prior art. While these units may be suitable for the particular purpose to which they address, they would not be as suitable for the purposes of the present invention as heretofore described.

FOCKE, HEINZ

POUCH MADE OF A SINGLE- OR MULTIPLE-PLY SYNTHETIC PLASTICS SHEET MATERIAL, PREFERABLY FOR TOBACCO

U.S. Pat. No. 3,510,053

The invention provides a pouch made of a single- or multiple-ply synthetic plastics sheet material, particularly polyethylene, for the reception of a material such as tobacco. The pouch is preferably formed by longitudinally folding over a continuous sheet of plastic material, so that it has a short wall and a longer wall which latter serves as a wrap-around flap. The pouch is sealed at three edges and has an opening sealed by a substantially air-tight closure so constructed that it can be easily torn open.

JERNBERG, GARY R.

PERIODONTAL BARRIER AND METHOD FOR AIDING PERIODONTAL TISSUE REGENERATION AGENTS

U.S. Pat. No. 5,197,882

A periodontal barrier and method incorporating chemotherapeutic agents is disclosed for aiding and guiding periodontal tissue regeneration.

PARKER, JONATHAN A.

INTRAORAL APPLIANCE

U.S. Pat. No. 5,267,862

Dental appliances formed using this method provide projections of the appliance itself which provide the necessary gripping forces rather than extraneous wires or other parts. The projections are formed by cutting grooves in casts of the teeth arches which will result in a projection, which will bear against the teeth, when the cast surface is duplicated in plastic. A first embodiment forms upper and lower plastic components, each having projections from the casts using the lost wax technique. These components are joined together in a predetermined relationship using a wax bit registration taken while the patient held his jaw in the predetermined relationship, and a dental articulator. A second method forms the plastic components directly over the casts. In this method the components are joined together, while mounted over the patient's arches, with the patient holding his jaw in the predetermined relationship. Both methods can be used to produce a single component with no joining of components then being required.

GAGLIO, THOMAS J.

SANTORIELLO, LUIGI

VISCOUS FLUID DISPENSING APPARATUS

U.S. Pat. No. 5,326,,685

This is an applicator for applying a viscous fluid to a surface. There is a flexible backing material of a closed-cell material and a flexible dispensing material of an open-celled material disposed over and carried by the flexible backing material. The open-celled material has an internal structural spacing sized relative to the viscosity of the fluid, so as to absorb and allow the fluid to slowly pass therethrough. Preferably, the flexible backing material and the flexible dispensing material are sealed together about the periphery thereof to form a hollow pocket. The fluid in the form of a gel, salve or the like, is disposed in the hollow pocket. The pocket can be filled with an oxidizing agent and used for tooth whitening and/or gum treatment. The pocket can be attached to an adhesive backing to make adhesive bandages which apply various medications to the underlying skin area. This approach can be employed for treating wounds and blemishes. The pockets can also be used for dispensing a variety of other materials including makeup remover, moisturizer, polishes, cleansers and the like.

SUMMARY OF THE INVENTION

A primary object of the present invention is to provide a gum growth pad that will overcome the shortcomings of the prior art devices.

Another object is to provide a gum growth pad that fits snugly and comfortably between the gums and buccal mucosa, since it does not buckle or rotate when in place and does not interfere with speech.

An additional object is to provide a gum growth pad that will deliver medication at a controlled rate directly onto the gums, by diffusing slowly through a semi-permeable membrane and into the saliva.

A still additional object is to provide a gum growth pad that is placed high up or low down, abutting the junction between the buccal mucosa and the gum, to allow greater contact between the medication and the gum tissue, with less likelihood of the medication being swallowed.

A further object is to provide a gum growth pad that is simple and easy to use.

A still further object is to provide a gum growth pad that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 1 is a perspective view of a head and upper torso of a person with parts broken away, showing the instant invention in dotted lines in place.

FIG. 2 is a front view taken, in the direction of arrow 2 in FIG. 1, with the exterior of the head shown in phantom.

FIG. 3 is a side view taken in the direction of arrow 3 in FIG. 2, showing the outline of the head complete.

FIG. 4 is an enlarged elevational view of the instant invention per se.

FIG. 5 is a side view taken in the direction of arrow 5 in FIG. 4.

FIG. 6 is a further enlarged cross sectional view taken along line 6—6 in FIG. 4, showing the internal structure thereof.

FIG. 7 is a diagrammatic cross sectional view taken along line 7—7 in FIG. 1, showing the positioning of the instant invention between the buccal mucosa and the gums of the teeth.

Similar reference characters denote corresponding features consistently throughout the attached drawings.

DETAILED DESCRIPTION OF THE PREFERRED EMBODIMENTS

Turning now descriptively to the drawings, in which similar reference characters denote similar elements throughout the several views, FIGS. 1 through 7 illustrate a gum growth pad 10 comprising a nonporous first layer 12 with an absorbent second layer 14 placed upon the nonporous first layer 12. A medication 16 in a liquid form is impregnated within the absorbent second layer 14 and then dried. A semi-permeable third layer 18 covers the absorbent second layer 14 with the dried medication 16. A facility 20 is for sealing the nonporous first layer 12 to the semi-permeable third layer 18 about a periphery thereof. The medication 16 is a gum tissue growth substance 21. The nonporous first layer 12 is applied high up or low down against the gum tissue 26 of the teeth 28 in the mouth of a person 24, with the semi-permeable third layer 18 against the buccal mucosa 22. Saliva in the mouth of the person 24 will penetrate through to the semi-permeable third layer 18 and cause the dried gum tissue growth substance 21 in the absorbent second layer 14 to liquify and diffuse through the semi-permeable third layer 18, to enhance the growth of the gum tissue 26, reverse age related gum recession, protect against gingival disease and loss of teeth 28. The nonporous first layer 12 contributes stability, but allows flexibility, so that the pad 10 can adapt to the cavity without buckling or curling.

As best seen in FIG. 3, the nonporous first layer 12 is a synthetic thermoplastic sheet 30. The absorbent second layer 14 is a sponge-like cushion 32. The semi-permeable third layer 18 is a thin membrane sheet 34. The sealing facility 20 is a hot-bond adhesive 36.

The gum growth pad 10, as best seen in FIGS. 4 and 5, has an elongated generally tubular shaped body 38 with bulb shaped ends 40, to supply a large posterior area of the gum tissue 26 and help stabilize placement between the buccal mucosa 22 and the gum tissue 26 of the teeth 28. The nonporous first layer 12 is flat, while the semi-permeable third layer 18 is curved on the tubular shaped body 38, so as to fit snugly and comfortably between the buccal mucosa 22 and the gum tissue 26 in the mouth of the person 24.

The gum tissue growth substance 21 can be a drug diphenylantoin sodium known as the trademark name DILANTIN, which is ordinarily used to treat and prevent seizures, with a well known side effect for gingival hyperplasia. DILANTIN has recently been shown to stimulate the formation of bone, as well as gum tissue.

The gum tissue growth medication 16 can also be an immuno-suppressant agent, such as cyclosporin or nifedipine. Immuno-suppressant agents are also known to stimulate gum growth. The gum tissue growth medication, 16 can also be a nerve growth factor, a protein gene product, or a bone growth protein. Bone growth protein stimulates the repair of bone and tooth-anchoring connective tissue. All these substances have the potential of preventing and treating periodontal disease.

OPERATION OF THE INVENTION

To use the gum growth pad 10, the following steps should be taken:

1. Apply the nonporous first layer 12 high up or low down against the gum tissue 26 of the teeth 28 in the mouth of the person 24.
2. Make sure that the semi-permeable third layer 18 is against the buccal mucosa 22.
3. The dried gum tissue growth substance 21 in the absorbent second layer will become liquified when saliva in the mouth of the person 24 penetrates through the semi-permeable third layer 18.
4. The liquified gum tissue growth substance 21 will diffuse through the semi-permeable third layer 18, to enhance the growth of the gum tissue 26.
5. The gum growth pad 10 will not interfere with speech and cause no discomfort.
6. Application of the gum growth pad 10, two to three times weekly, will regenerate the tooth anchoring connective gum tissue 26 to help protect against gingival disease.

LIST OF REFERENCE NUMBERS 10 gum growth pad
12 nonporous first layer of 10
14 absorbent second layer of 10
16 medication of 10 in 14
18 semi-permeable third layer of 10
20 sealing facility of 10
21 gum tissue growth substance for 16
22 buccal mucosa of 24
24 person
26 gum tissue of 24
28 teeth of 24
30 synthetic thermoplastic sheet for 12
32 sponge-like cushion for 14
34 thin membrane sheet for 18
36 hot-bond adhesive for 20
38 elongated generally tubular shaped body for 10
40 bulb shaped end on 38

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A gum growth pad comprising:
   a) a nonporous first layer;
   b) an absorbent second layer placed upon and in contact with said nonporous first layer;
   c) a dried medication capable of being liquified by saliva impregnated within said absorbent second layer;
   d) a semi-permeable third layer covering said absorbent second layer with said dried medication forming a pocket completely filled by said absorbent second layer; and
   e) means for sealing said nonporous first layer to said semi-permeable third layer about a periphery thereof.

2. A gum growth pad as recited in claim 1, wherein said medication is a gum tissue growth substance, whereby said nonporous first layer is applied high up/low down against the gum tissue of the teeth in the mouth of a person, with said semi-permeable third layer against the buccal mucosa, so that saliva in the mouth of the person will penetrate through to said semi-permeable third layer and cause said dried gum tissue growth substance in said absorbent second layer to liquify and diffuse through said semi-permeable third layer, to enhance the growth of the gum tissue, reverse age related gum recession, protect against gingival disease and loss of teeth, wherein said nonporous first layer contributes stability, but allows flexibility, so that said pad can adapt to the cavity without buckling and curling.

3. A gum growth pad as recited in claim 1, wherein said nonporous first layer is a synthetic thermoplastic sheet.

4. A gum growth pad as recited in claim 1, wherein said absorbent second layer is a sponge cushion.

5. A gum growth pad as recited in claim 1, wherein said semi-permeable third layer is a thin membrane sheet.

6. A gum growth pad as recited in claim 1, wherein said sealing means is a hot-bond adhesive.

7. A gum growth pad as recited in claim 1, further having an elongated generally tubular shaped body with bulb shaped ends, to supply a large posterior area of the gum tissue and help stabilize placement between the buccal mucosa and the gum tissue of the teeth.

8. A gum growth pad as recited in claim 7, wherein said nonporous first layer is flat, while said semi-permeable third layer is curved on said tubular shaped body, so as to fit snugly and comfortably between the buccal mucosa and the gum tissue in the mouth of the person.

9. A gum growth pad as recited in claim 2, wherein said gum tissue growth substance is a drug diphenylhydantoin sodium, which is ordinarily used to treat and prevent seizures, with a well known side effect for gingival hyperplasia, whereby drug diphenylantoin soduim stimulates the formation of bone, as well as gum tissue.

10. A gum growth pad as recited in claim 2, wherein said gum tissue growth substance is an immuno-suppressant agent, such as cyclosporin and nifedipine that will stimulate gum growth.

11. A gum growth pad as recited in claim 2, wherein said gum tissue growth substance is a nerve growth factor.

12. A gum growth pad as recited in claim 2, wherein said gum growth substance is a protein gene product.

13. A gum growth pad as recited in claim 2, wherein said gum tissue growth substance is a bone growth protein that will stimulate the repair of bone and tooth-anchoring corrective tissue.

14. The method of delivering medication at a controlled rate directly onto human tissue within the mouth of a person utilizing a pad, said pad consisting essentially of a nonporous first layer, an absorbent second layer on one side of said nonporous first layer, and a semi-permeable third layer covering the absorbent second layer forming a sealed pocket completely filled with said absorbent second layer, said method comprising the steps of:
   a) impregnating said absorbent second layer with medication in a liquid form and then drying said medication; and
   b) placing said pad within the mouth of said person with the semi-permeable third layer in contact with the tissue to receive said medication for permitting the saliva within said mouth to penetrate said semi-permeable third layer causing the dried medication to liquify and diffuse through said semi-permeable third layer.

15. The method of claim 14 in which said pad is placed between the buccal mucosa and the gum tissue in said mouth.

16. The method of claim 15 in which said medication is diphenylantoin sodium.

17. The method of claim 15 in which said pad includes means for stabilizing said pad within said mouth.

18. The method of claim 17 in which said stabilizing means comprises said pad having a generally tubular shaped body with the first layer being flat and having bulb shaped ends.

* * * * *